United States Patent [19]
Shockey

[11] Patent Number: 5,168,864
[45] Date of Patent: Dec. 8, 1992

[54] DEFLECTABLE ENDOSCOPE
[75] Inventor: Rick L. Shockey, Coon Rapids, Minn.
[73] Assignee: Clarus Medical Systems, Inc., Plymouth, Minn.
[21] Appl. No.: 765,989
[22] Filed: Sep. 26, 1991
[51] Int. Cl.$^5$ .............................................. A61B 1/00
[52] U.S. Cl. ........................................ 128/4; 128/6; 604/280; 604/282
[58] Field of Search ............... 128/4, 6; 604/280, 282

[56] References Cited
U.S. PATENT DOCUMENTS

| | | |
|---|---|---|
| 3,528,406 | 9/1970 | Jeckel . |
| 4,245,624 | 1/1981 | Komiya . |
| 4,586,923 | 5/1986 | Gould et al. . |
| 4,723,939 | 2/1988 | Anaise . |
| 4,758,221 | 7/1988 | Jureidini . |
| 4,817,613 | 4/1989 | Jaraczewski et al. ......... 604/282 X |
| 4,822,345 | 4/1989 | Danforth . |
| 4,898,577 | 2/1990 | Badger et al. . |
| 4,911,148 | 3/1990 | Sosnowski et al. . |
| 4,960,411 | 10/1990 | Buchbinder . |

FOREIGN PATENT DOCUMENTS 8909079  5/1989  World Int. Prop. O. .......... 604/282

Primary Examiner—Theatrice Brown
Assistant Examiner—J. Doyle
Attorney, Agent, or Firm—Haugen and Nikolai

[57] ABSTRACT

An improved endoscope having a flexible tip portion with both a selectable angle of deflection, and a selectable radius of curvature to provide a more maneuverable endoscope for use by a physician. It includes a body member receiving a rigid tube within a lumen thereof. The tube extends toward, but short of the distal end of the body member to define a deflectable tip portion. A pull-wire is positioned within the rigid tube and lumen and extends from the body member's proximal end to the body member's distal end. By selectively retracting the pull-wire in the proximal direction, the distal end of the flexible tip portion is deflected about the distal end of the rigid tube. In an alternative embodiment of the invention, a second rigid tube is telescopingly received within the first rigid tube. The second tube is selectively extendable beyond the distal end of the first rigid tube into the lumen of the body member. In this manner, the length of the flexible tip portion of the endoscope is selectable to determine a radius of curvature of the flexible tip portion as well.

11 Claims, 3 Drawing Sheets

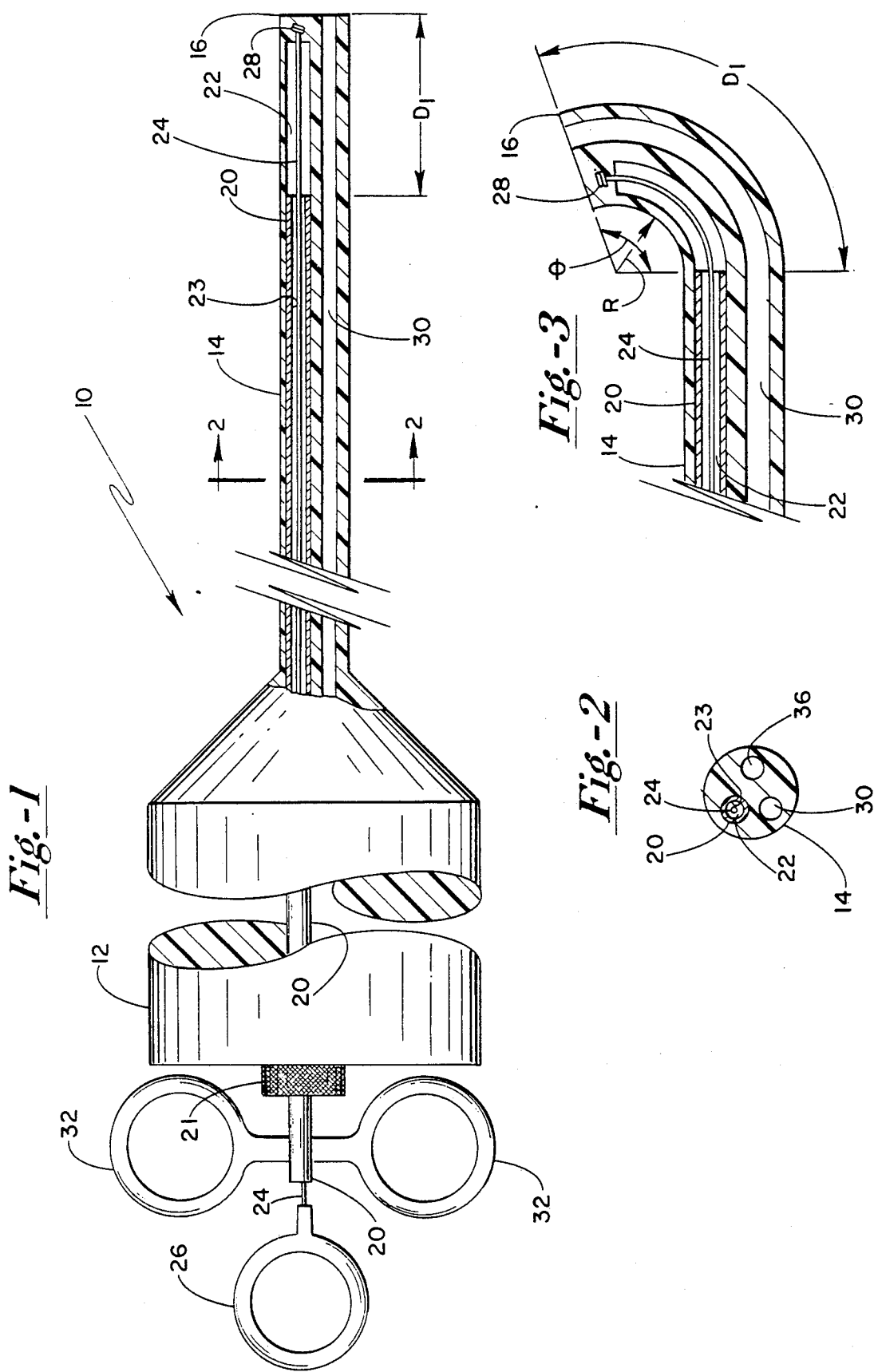

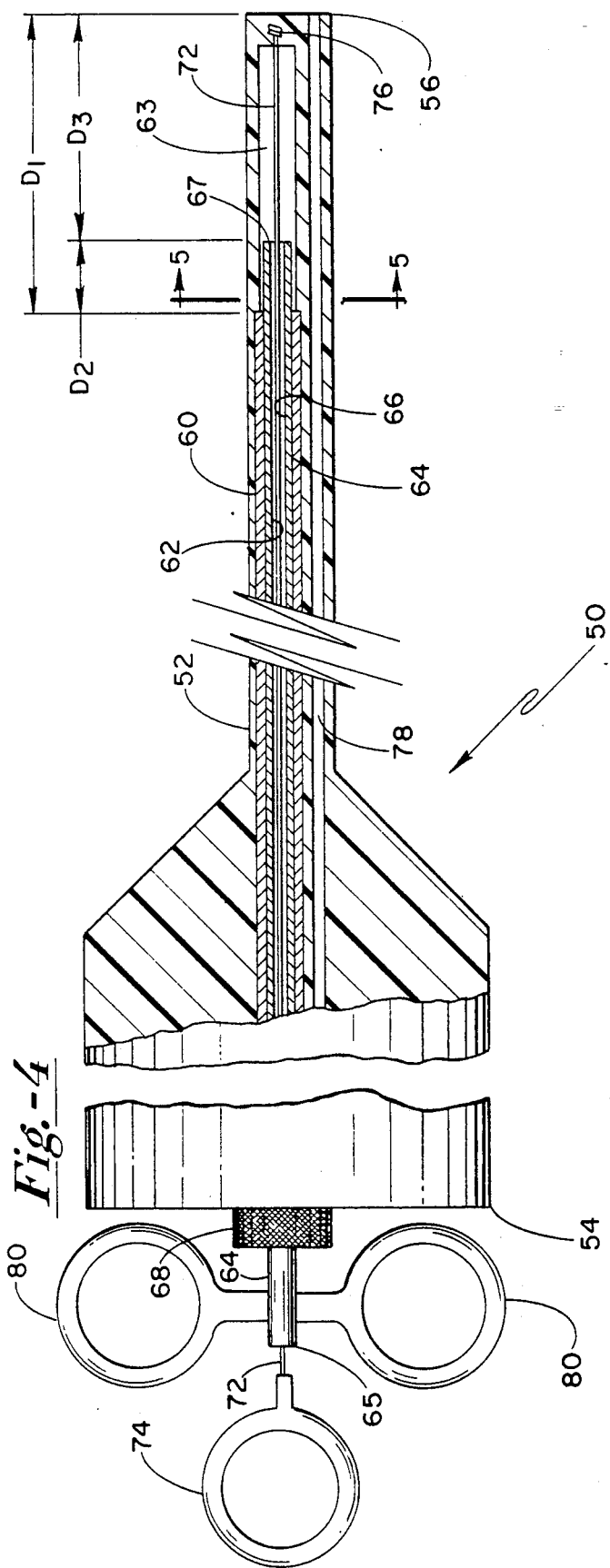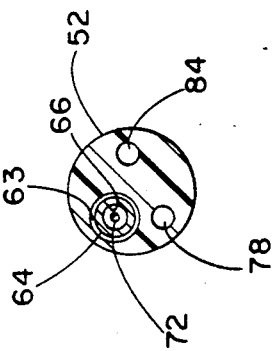

DEFLECTABLE ENDOSCOPE

BACKGROUND OF THE INVENTION

I. Field of the Invention

This invention relates generally to surgical and diagnostic endoscopes and, more particularly, to an endoscope with a selectively deflectable tip portion to facilitate maneuvering or steering of the distal end thereof.

II. Discussion of the Prior Art

In performing a variety of surgical procedures without a major incision, a surgeon typically may use an endoscope having several lumens therewithin providing flush ports, suction ports, a passageway for routing a first optical fiber for illuminating and another for conveying the image and frequently, but not necessarily, a working lumen for allowing another instrument to be passed therethrough. A light source is usually placed at the proximal end of the illumination fiber to illuminate the internal area being operated upon. An optical image is transmitted back through the endoscope, via the image optical fibers, to aid the surgeon during the operation. Endoscopes having a rigid sheath are adapted to be maneuvered by the surgeon exterior of the patient to locate the distal end proximate the selected tissue. The distal end, then, is finely positioned to locate it adjacent the tissue to be examined or operated upon, at which point a surgical instrument disposed in the working lumen may be activated.

Various endoscopes are known in the art having steerable distal tips. Generally speaking, the maneuverability these endoscopes provide the surgeon with only a limited ability to conveniently maneuver the distal tip. Some instruments have a limited rotation angle which is less than 180 degrees. This limitation prevents access to a wall adjacent an opening through which the endoscope is inserted. Others have a radius of curvature which is fixed, thus restricting the accessibility of the distal tip to the tissue without significant efforts of the surgeon maneuvering of the endoscope exterior to the patient. Excessive maneuvering of the endoscope exterior of the patient is frustrating, time consuming, and inefficient to the surgeon performing a delicate operation.

U.S. Pat. No. 4,245,624, issued to Komiya, teaches a flexible tube section projecting out from the distal end of an endoscope. A wire is located exterior to the flexible portion and is bridged from the distal end of the endoscope to the end of the flexible portion. While providing the ability to steer the flexible end portion, this wire inhibits the maneuverability of the flexible portion in tight and delicate locations of the patient. Further, the length of the flexible portion is not selectable.

U.S. Pat. No. 4,586,923, issued to Gould et al., shows a catheter with a curving distal tip. The exterior sheath of the catheter is stiff, but an extending tip is flexible. A wire located within a lumen and connected to the flexible tip causes the tip to flex when retracted. The flexible portion of this catheter is a fixed length, thus defining a radius of curvature which may prove to be either too large or too small, depending on the operation being performed by the surgeon.

U.S. Pat. No. 4,960,41, issued to Buchbinder, teaches a steerable catheter substantially enclosed in a catheter shell. The flexible distal tip portion of the catheter is not adjustable in length, hence, the radius of curvature of the tip is not selectable. Rather, only the angle of deflection is selectable. The use of this instrument would be limited in some procedures where the radius and length of the flexible tip requires adaptation to a particular body cavity. Further, the desirable tip size typically would not be known until the tip is inserted into the patient proximate the desired tissue. Trial and error during surgery is time consuming and frustrating.

U.S. Pat. No. 4,898,577, issued to Badger et al., teaches a guiding catheter with a controllable distal tip having articulated sections. The deflection of the distal tip is not continuous, and the radius of curvature is not selectable. Hence, the maneuverability of the guiding catheter is somewhat limited for surgical procedures in a very small cavity.

OBJECTS

It is accordingly a principle object of the present invention to provide an improved endoscope with a flexible, deflectable tip.

Another object of the present invention is to provide an endoscope with a flexible, tip which can be selectively deflected up to 180 degrees, with the radius of curvature being also selectable. The endoscope preferably will have a substantially rigid shaft leading to the flexible tip, wherein the flexible tip can be selectively maneuvered within very small body cavities of the patient during an operation. The endoscope should be easy to use and highly maneuverable to facilitate a successful surgical operation.

SUMMARY OF THE INVENTION

The foregoing objects and advantages of the invention are achieved by providing an endoscope with a maneuverable, flexible distal tip. The endoscope includes a tubular and flexible body member having a distal end, a proximal end, and a first lumen extending longitudinally therebetween. A first rigid guide tube is received within the first lumen of the body member and extends from the proximal end thereof to a predetermined location proximal of the body member distal end. The portion of body member extending beyond the distal end of the first rigid guide tube defines a flexible tip portion of the body member. A pull-wire is located within the first lumen and is fixedly connected to the body member's distal end. Upon pulling the pull-wire in the proximal direction, the body member's distal end is caused to bend at the transition between the distal end of the first rigid guide tube and the flexible end portion of the tubular body member. The first rigid guide tube preferably is formed from stainless steel, although other metals or a rigid plastic may be used as well.

In a further improvement of the invention, the first lumen is located off-center and closely proximate the outer surface of the body member. The first rigid guide tube is selectively extendable within the lumen of the body member to selectively define the length of the flexible tip portion of the instrument. The length of the flexible tip portion is proportional to the defined radius of curvature when the distal tip is deflected.

In an alternative embodiment of the invention, the first rigid guide tube telescopingly receives a second rigid guide tube which is selectively extendable within and beyond the distal end of the first rigid guide tube. By selectively telescoping the second rigid guide tube within the first rigid guide tube, the length of the flexible tip at the distal end of the body member is selectively determined. Thus, the radius of curvature of the flexible portion of the body member is selectively reduced as the second rigid guide tube is extended toward the body member's distal end. When the second rigid tube is fully extended in the distal direction, substantially no flexible portion remains at the body member distal end and it becomes substantially rigid over the entire length. In contrast, when the second rigid tube is substantially retracted within the first rigid tube, a longer flexible tip is defined wherein the radius of curvature of the deflected body member's distal end is substantially larger for maneuvering in a large cavity of the patient. Preferably, the second rigid guide tube also may be formed of stainless steel, other metals or plastic.

The telescoping feature of the alternative embodiment allows the surgeon to selectively define the length of the distal flexible tip to determine a radius of curvature during deflection.

Other objects, features, and advantages of the invention will become apparent to those skilled in the art from the following detailed description of a preferred embodiment, especially when considered in conjunction with the accompanying drawings in which like numerals in the several views refer to corresponding parts.

BRIEF DESCRIPTION OF THE DRAWINGS

FIG. 1 is a partial sectional planar view of an endoscope having a slidably received first rigid guide tube reinforcing its tubular, flexible body and receiving a pull-wire according to the preferred embodiment of the present invention;

FIG. 2 is a sectional view taken along the line 2—2 in FIG. 1 and illustrating several adjacent lumens;

FIG. 3 is a partial longitudinally sectioned view of the distal tip of the preferred embodiment;

FIG. 4 is a partial, longitudinally sectional view of an alternative embodiment of the present invention in which a second rigid tube is telescopingly received within a first rigid tube is;

FIG. 5 is a sectional view taken along line 5—5 in FIG. 4 illustrating several adjacent lumens and the second rigid tube received within a lumen;

DESCRIPTION OF THE PREFERRED EMBODIMENT

Figure 6:
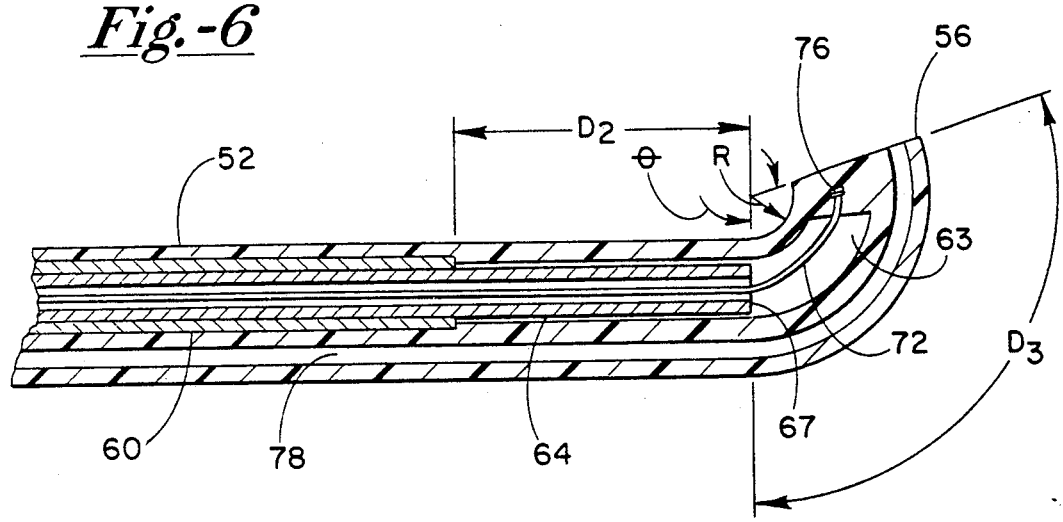
FIG. 6 is a partial, longitudinally sectioned view of the alternative embodiment illustrating a short flexible tip having a small radius of curvature.

Referring to FIG. 1., an endoscope according to the present invention is generally shown at 10. Endoscope 10 includes a large diameter proximal end 12 forming a handle bonded to a tubular body member 14 comprised of a flexible medical-grade plastic or polymer extending to a smaller diameter distal end 16. A relatively rigid, stainless steel tube 20 is coaxially received within a lumen 22 defined in body member 14 and extends from exterior of proximal end 12 to a selectable distance $D_1$ from distal end 16. Distance $D_1$ defines the length of a flexible tip portion of body member 14. Tube 20 extends through a Touhy-Borst type clamp 21 and when released is axially rotatable 360 degrees and longitudinally slidable within lumen 22 the entire length thereof. Lumen 22 is preferably located off-center of body member 14, closely proximate an outer wall surface of body member 14. Tube 20 has an inner lumen 23 opening to the distal segment of lumen 22 in body member 14. A pull-wire 24 extends from a pull-wire loop 26 located exterior of proximal end 12 of the handle, through the lumen 23 of the guide tube and lumen 22 of the flexible body member 14, and terminates at point 28 within a distal wall of body member 14. Attachment point 28 may be reinforced with an adhesive, such as epoxy.

Upon retracting loop 26 in a proximal direction, the flexible tip portion of distal end 16, defined as distance $D_1$, bends or curls about the distal end of tube 20, as will be described in detail shortly. Body member 14 also includes several other lumens including a second lumen 30 extending from proximal end 12 to an opening at distal end 16. Lumen 30 can function as a flush port or a passageway for an optic fiber used to transmit video images; however, limitations to the use of lumen 30 is not to be inferred. Moreover, the body member may include additional lumens for allowing other optical fibers or working instruments to be inserted therethrough.

A pair of finger loops 32 are integrally formed or otherwise attached at the proximal end of rod 20. Loops 32 serve as a leverage point when retracting finger loop 26 in a proximal direction to bend the flexible tip portion of length $D_1$ at distal end 16.

Referring to FIG. 2, a transverse sectional end view taken along line 2—2 in FIG. 1 is illustrated to show tube 20, lumen 22, cavity 23 and pull-wire 24, all concentrically arranged. As mentioned above, body member 14 can include several other lumens, such as lumen 36, to provide other functions, such as suction for aspirating debris from distal end 16 or for another purpose.

Now referring to FIG. 3, deflection of distal end 16 is illustrated. By selectively retracting thumb loop 26 in a proximal direction to retract pull-wire 24, the length of wire 24 extending beyond the distal end of tube 20 is shortened causing the flexible distal portion of length $D_1$ to curl. Distal end 16 curls about the distal end of tube 20 and the radius of curvature is proportional to the length of wire 24 retracted in the proximal direction from lumen 22. As more wire 24 is retracted in the proximal direction from lumen 22, the arcuate curvature represented as angle $\theta$ of distal end 16 proportionally increases. Since rigid tube 20 is off-center from the longitudinal axis of body member 14 and is disposed closely proximate the outer surface of body member 14, distal end 16 deflects about the distal end of tube 20 toward this proximate surface. Angle $\theta$ is variable and proportional to the amount of wire 24 retracted in the proximal direction through lumen 22. Since body member 14 is formed of a sufficiently flexible plastic material, distal end 16 of length $D_1$ can bend at least 180 degrees back toward proximal end 12.

Tube 20 is slidably received within body member 14, hence, distance $D_1$ is a selectable distance. The flexible distal portion of length $D_1$ proportionally defines a selectable radius of curvature, R, when deflected. Thus, the larger the distance $D_1$, the larger the radius R. This allows the physician to selectively adjust and adapt the radius R of the flexible tip portion while received within a body cavity.

This preferred embodiment of the present invention provides an endoscope having a conveniently deflectable distal end which is simpler to manufacture than prior art steerable endoscopes. This selectable deflection $\theta$ and selectable radius, R, of distal end 16 allows the surgeon to selectively place and adaptably maneuver distal end 16 during surgery, such as within a cavity of an organ being operated on.

ALTERNATIVE EMBODIMENT

An alternative embodiment of a deflectable endoscope is illustrated in FIG. 4 and generally labeled 50. Endoscope 50 includes a body member 52, similar to body member 14 in the earlier described embodiment, and is formed from a suitable flexible, medical-grade plastic. It has a handle at its proximal end 54 and its proximal end is identified by numeral 56. Lumen 63 extends from the distal end 54 and terminates at distal end 56. A first, rigid, stainless steel tube 60, having an inner wall surface 62, is fixedly received within first lumen 63 extending from proximal end 54 to a predetermined distance labeled $D_1$ short of the distal end 56. A second stainless steel rigid tube 64 is coaxially and slidably received within first tube 60 and conforms to inner surface 62. Second tube 64 extends from a proximal end 65 exterior of body member proximal end 54 to a distal end 67. Distal end 67 is selectively and slidably positionable within the narrower distal segment of lumen 63 of the body member. The combination of first and second tubes 60 and 64, respectively, reinforces body member 54 the corresponding length. A pull-wire 72 comprised of a pliable wire such as stainless steel, resides in the lumen 66 of the second tube 62. Pull-wire 72 extends from a handle loop 74 exterior of second tube proximal end 65, through cavity 66 and lumen 63, and is securably fastened within body member proximal end 56 at point 76. Point 76 is closely proximate an outer distal surface of body member 14. A second lumen 78 is also integrally formed within body member 50 and extends from proximal end 54 to distal end 56. Lumen 78 can serve various functions, such as a flush port, an aspiration port, a working channel or a path for an optic fiber transmitting light or video images.

Second tube 64 is selectively extendable within first tube 60 and lumen 63 in a telescoping manner by gripping a pair of handle loops 80 secured to second tube proximal end 65 and motioning thumb loop 74 of second tube 64 in a longitudinal direction. Second tube 64 is releasably secured within first tube 60 by twisting a Touhy-Borst type clamp 68 received in proximal end 54. In this way, the degree of distal end 67 beyond that of tube 64 is selectable distance, $D_2$. The length of body member 52 extending beyond the distal end 67 of the second tube is substantially flexible. To selectively deflect flexible portion of length $D_3$, the surgeon retracts thumb loop 74 in the proximal direction. This retraction shortens the length of wire 72 extending past the second tube's distal end 67.

Referring to FIG. 5, a sectional view taken along line 5—5 in FIG. 4 is shown to illustrate the manner in which the second tube 64 is slidably received within lumen 63. A third lumen 84, similar to lumen 78, is shown which can serve as a suction passage or the like.

Figure 7:
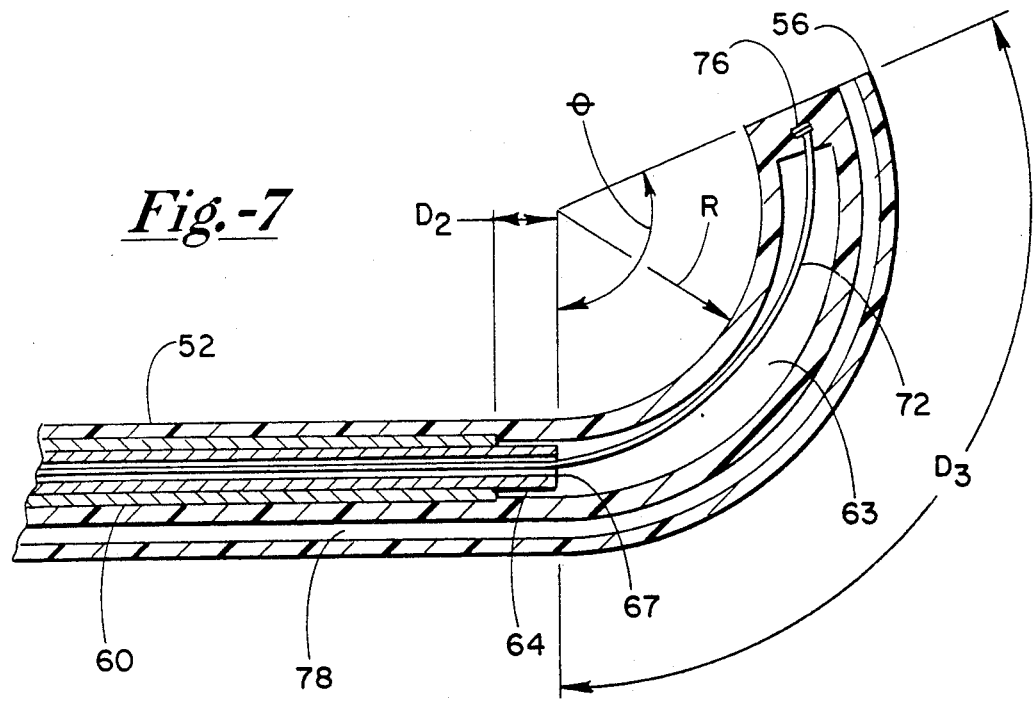
FIG. 7 is a partial, longitudinally sectioned view of the alternative embodiment illustrating a long flexible tip having a larger radius of curvature in contrast to FIG. 6.

Now, referring to FIGS. 6 and 7, adjustable distance, $D_2$, determines distance, $D_3$, which represents the flexible length of body member 52 at distal end 56. Selectable length, $D_3$, determines a radius, labeled R, of distal end 56 when deflected. First, FIG. 6 illustrates second tube 64 extending a substantial distance past the distal end of first tube 60 to define a relatively small flexible segment of length, $D_3$, at distal end 56. When the physician retracts pull-wire 72 in a proximal direction, thus shortening the length of wire 72 extending beyond second tube distal end 67, distal end 56 bends about second tube distal end 67. The angle of deflection $\theta$ proportionally increases as wire 72 is retracted in the proximal direction wherein the radius of curvature R is substantially small. Because flexible portion, $D_3$, is relatively short, a small increment of retracting wire 72 creates a large deflection $\theta$ of distal end 56. Thus, distal end 56 can be curved with a small radius to maneuver within a small cavity.

Next, referring to FIG. 7, in contrast, second tube distal end 67 extends a relatively short distance $D_2$ past the distal end of first tube 64. Thus, a substantially long flexible segment of distal end 56 of length $D_3$ is defined. Here, when wire 72 is selectively retracted in the proximal direction, distal end 56 of length $D_3$ bends about second tube distal end 67 to create a substantially larger radius of curvature labeled R. This allows the surgeon to bend the flexible portion of length $D_3$ a further distance from the longitudinal axis of body member 52 to conveniently reach a wall of a cavity being operated on.

Thus, as illustrated by FIGS. 6 and 7, both the radius of curvature, R, and the degree of deflection, $\theta$, is easily selectable by the surgeon. The more wire 72 is retracted, the larger the deflection angle $\theta$ of the flexible segment of distal end 56. The further second tube distal end 67 is telescopingly positioned past the distal end of first tube 60, the smaller the radius of curvature, R. Thus, the surgeon can vary the deflection of distal end 56 to maneuver in both small and large cavities in a convenient manner.

In summary, tube 20 described in the preferred embodiment, and first and second tubes 60 and 64 in the alternative embodiment, are positioned in a first lumen to provide rigid longitudinal support for body member 14 of corresponding length. The portion of the body member's distal end extending past the respective rigid tube is the flexible portion of the body member. The more pull-wire retracted in a proximal direction, the larger the deflection angle $\theta$ of the flexible portion achieved to locate the body member distal end proximate the wall of the cavity undergoing surgery. The endoscope includes several other lumens which can serve as flush ports, suction passageways, and passageways for routing video images from the endoscope proximal end. Thus, the endoscope described is adapted to be multi-functional and versatile to allow the surgeon an increased maneuverability during surgery.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An endoscope, comprising:
   (a) a tubular, generally flexible body member having a distal end, a proximal end, and a first lumen extending therebetween;
   (b) a tubular, generally rigid first guide tube means having a distal end and received within said first lumen for reinforcing said body member over the length of said first guide tube means, said first guide tube means extending from said body member's proximal end toward, but short of, said distal end of said body member and being longitudinally slidable within said first lumen, said first guide tube means defining a flexible portion of said body member between said distal end of said guide tube means and said distal end of said body member; and (c) a pull-wire for manipulating said body member's distal end, said pull-wire being disposed within said first lumen and extending from said proximal end of said body member to a point fixedly connected to said body member's distal end such that tensioning said pull-wire in a proximal direction causes said flexible portion of said body member to bend about said distal end of said first guide tube means.

2. The endoscope as specified in claim 1 wherein said first lumen is off-center of said body member.

3. The endoscope as specified in claim 1 wherein said first rigid guide tube means comprises stainless steel.

4. The endoscope as in claim 1 further comprising a tubular and generally rigid second guide tube means telescopingly received within said first guide tube means and relatively movable longitudinally therein, said second guide tube means extending a selectable distance beyond said distal end of said first guide tube means into said first lumen for reducing the length of said flexible portion of said body member.

5. The endoscope as specified in claim 4 wherein said second rigid guide tube means comprises stainless steel.

6. The endoscope as specified in claim 4 wherein said first lumen terminates a predetermined distance from said body member's distal end.

7. The endoscope as specified in claim 6 wherein said pull-wire has a distal end terminating in said body member's distal end.

8. The endoscope as specified in claim 1 wherein said body member further includes a second lumen extending from said body member's proximal end to said body member's distal end.

9. The endoscope as specified in claim 4 wherein said body member further includes a second lumen extending from said body member's proximal end to said body member's distal end.

10. The endoscope as specified in claim 1 further comprising clamping means disposed at the proximal end of said first guide tube means for releasably restraining said first guide tube means from longitudinal movement within said body member.

11. The endoscope as specified in claim 4 further comprising a clamping means disposed at the proximal end of said second guide tube means for releasably securing said second guide means within said first guide tube means.

* * * * *